United States Patent [19]
Gast et al.

[11] Patent Number: 5,171,995
[45] Date of Patent: Dec. 15, 1992

[54] SAMPLE HOLDER FOR OPTICAL SPECTROMETER AND METHOD FOR TAKING A SPECTRUM

[75] Inventors: Jürgen Gast, Rheinstetten; Arno Simon, Karlsruhe-Waldstadt; Eckhard Reh, Hüglfing, all of Fed. Rep. of Germany

[73] Assignee: Bruker Analytische MeBtechnik GmbH, Fed. Rep. of Germany

[21] Appl. No.: 764,619

[22] Filed: Sep. 24, 1991

[30] Foreign Application Priority Data

Sep. 28, 1990 [DE] Fed. Rep. of Germany ....... 4030699

[51] Int. Cl.$^5$ .............................. G01N 21/01
[52] U.S. Cl. ..................... 250/339; 356/244
[58] Field of Search .......... 356/440, 244, 246; 250/341, 339

[56] References Cited

U.S. PATENT DOCUMENTS

| | | | |
|---|---|---|---|
| 4,619,530 | 10/1986 | Meserol et al. | 356/440 |
| 4,673,289 | 6/1987 | Gaucher | 356/72 |
| 4,956,150 | 9/1990 | Henry | 356/244 |

FOREIGN PATENT DOCUMENTS

| | | | |
|---|---|---|---|
| 0254246 | 7/1987 | European Pat. Off. | |
| 208439 | 12/1982 | Japan | 356/246 |

Primary Examiner—Carolyn E. Fields
Attorney, Agent, or Firm—Walter A. Hackler

[57] ABSTRACT

A sample holder for placing a sample substance for transmission measurements with optical radiation into a spectrometer, in particular, a FTIR spectrometer which is at least partially made from a material transparent to the optical radiation in an intermeshing wavelength region and which exhibits an index of refraction in excess of 1 is configured as a converging lens with a concave surface (11) and a convex surface (12). To take an absorption spectrum of a powder and/or fluid dissolved or suspended sample substance, the sample substance is brought onto the concave surface (11) of the sample holder before the measurement where it, in consequence of the curvature and in contrast to a flat surface, is concentrated in a substantially smaller surface region. The configuration of the sample holder as a converging lens increases the yield of the radiation penetrating through the sample substance onto the detector of the spectrometer configuration.

18 Claims, 5 Drawing Sheets

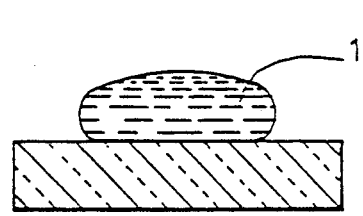
Fig.1a (PRIOR ART)
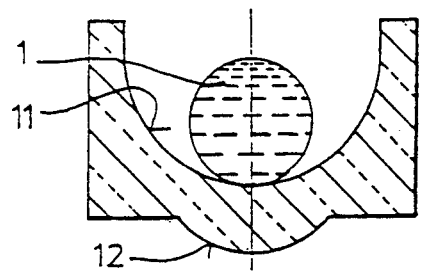
Fig.1d
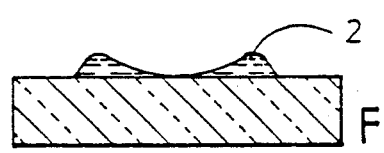
Fig.1b (PRIOR ART)
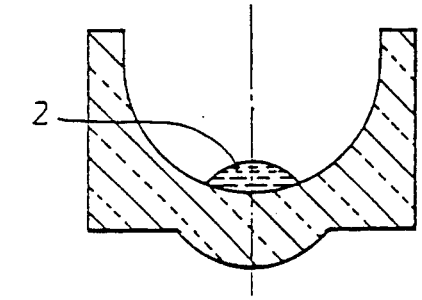
Fig.1e
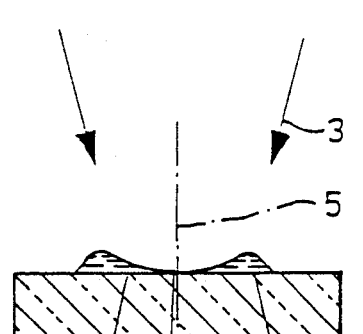
Fig.1c (PRIOR ART)
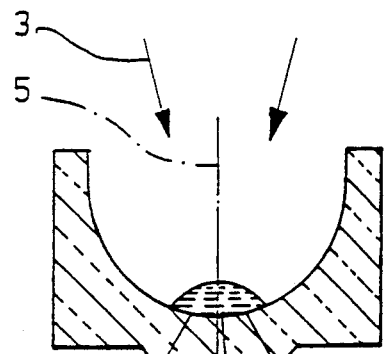
Fig.1f
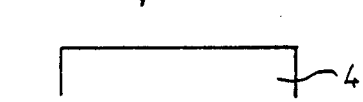

SAMPLE HOLDER FOR OPTICAL SPECTROMETER AND METHOD FOR TAKING A SPECTRUM

BACKGROUND OF THE INVENTION

The invention concerns a sample holder for the introduction of a sample substance for transmission measurements with optical radiation into a spectrometer, in particular, an infrared spectrometer said sample holder being at least partially made from a material which is transparent in an interesting wavelength region of the optical radiation and exhibiting an index of refraction in excess of 1.

Such a sample holder is, by way of example, known in the art from the article 459 of A. M. Haefner et al. in the Book of Abstracts of the Pittsburgh Conference from Mar. 6, 1989 through Mar. 10, 1989 in Atlanta, USA. The sample holder which is known in the art consists of an approximately plane parallel plate upon which a sample substance initially dissolved in a solvent, which, by way of example is taken from a chromatograph, is deposited in the form of a drop. One then allows the solvent to vaporize or to evaporate so that a layer of the sample substance remains, in powder form, on the sample holder which is examined in diffuse transmission. A disadvantage of the procedure which is known in the art is, when introducing the drop onto the flat sample holder, the solvent spreads out over the surface of the sample holder and after evaporation or vaporization of the solvent the sample substance is distributed over a relatively large surface area, whereby there is moreover a tendency for the sample substance to accumulate largely on the borders of the deposited liquid where it is therefore present in substantially higher concentrations than in the middle of the deposited drop. In particular, if the plane parallel surfaces are not kept exactly horizontal when introducing the drop onto the sample holder then the fluid with the sample substance can spread over the surface of the sample holder and thereby distribute itself over a still larger surface area. Furthermore, a great amount of light is lost in the subsequent transmission measurement in that, after passing through the surface containing the sample substance, said light is emitted at large angles from the optical axis of the ray path.

Known in the art from the article 249 of K. H. Shafer et al. in the Book of Abstracts of the Pittsburgh Conference in Atlantic City, USA, from Mar. 10, 1986 through Mar. 14, 1986 is a procedure with which the sample substance is introduced onto an infrared transparent powder, by way of example KCI, diamond or glass located in a cup-shaped depression of an aluminium strip. A spectrum of the sample substance is subsequently taken in diffuse refraction. A disadvantage of this method is that the reflection measurement requires an extensive set-up and is less sensitive and also less reproducible than a transmission measurement.

SUMMARY OF THE INVENTION

Therefore it is the object of the present invention to introduce a sample holder of the above mentioned kind which allows for the sample substance to be concentrated into as small a surface area as possible and bunches as much of the radiated light intensity passing through the sample substance as possible about the optical axis of a spectrometer in order to take as intense a spectrum as possible.

This object is achieved in accordance with the invention in that the sample holder is configured as a converging lens with a concave surface and a convex surface. When taking a transmission spectrum, the sample holder is so positioned that the strongly curved convex surface is pointed in the direction of the detector whereas the less strongly curved concave surface of the sample holder holds the sample substance. In this manner the sample substance concentrates itself at the deepest position of the concave surface so that a substantially higher density of the sample substance is distributed over a substantially smaller surface area than is the case in the conventional flat sample holders. When irradiating the sample holder, the light emanating out of the sample substance is refracted towards the optical axis of the configuration through the focussing properties of the converging lens. In this manner more light from the sample reaches the detector than would have been the case with a flat window. The curvature of the concave surface, during the introduction and possible vaporization or evaporation, therefore initially effects a concentration of the sample substance, and in combination with the stronger curved convex surface, a partial focussing of the light leaving the sample substance in the direction of the spectrometer configuration detector.

In a conventional optical spectrometer images are effected upon a slit-shaped aperture. In order to match the sample holder in accordance with the invention to the slit-shaped image geometry, the sample holder, in one embodiment of the invention, is configured as a cylinder lens. In this case, the concave surface is preferentially a cylindrically curved groove. In this fashion an improvement of the light yield with respect to that of a flat sample holder is already achieved, however, a convergence of the light is only effected in one radiation direction, that is to say, perpendicular to the cylinder axis. As viewed from the direction of the cylinder axis, a diverging portion of the incident radiated light cannot be refracted back onto the optical axis which, in turn, is approximately perpendicular to said cylinder axis. In this fashion the advantageous properties of the sample holder in accordance with the invention can only be utilized in one dimension.

In particular in connection with chromatography the sample holder can in this way be very long, e.g. similar to the groove on a record, which allows depositing and measuring the output of the chromatograph continuously.

In a particular preferred embodiment the sample holder is configured as a lens which is rotationally symmetric with respect to the optical axis. In this manner the light penetrating through the sample holder is concentrated at a point. This point must not invariably coincide with the focal point of the converging lens, however, in practice, should be as close as possible to this point so that the light passing through the sample holder if not parallel then is at least less divergent than is the case with a flat window emergence. This embodiment of the invention permits an optimal matching to a spectrometer type with a circularly round aperture and allows for as large a concentration of the incident light onto the sample substance as possible. Since, with the sample holder in accordance with the invention, the sample substance is already present on the concave surface in a substantially more concentrated surface area as is the case with a flat sample holder, it is thereby possible to focus the light incident upon the sample to nearly a point.

This is particularly advantageous for the case of a Fourier Transform spectrometer with which the optical imaging is onto a circular surface area. Through the rotational symmetry of the sample holder, due to the, in real cases, still plane-like extension of the sample substance, an improved illumination of the sample substance which, in general, is present in very small concentrations, is achieved and therewith a substantial improvement in the signal. In a preferred embodiment, the sample holder in accordance with the invention is constructed from a solvent resistant material. Preferentially, the sample holder is constructed at least partially from ZnSe which, with an index of refraction of 2.3, effects a sufficiently strong convergence of the light beams emerging from the sample holder towards the optical axis, while exhibiting reflection losses of only 30%.

In a particularly preferred embodiment, the concave and the convex surfaces of the sample holder are polished. Such highly polished surfaces can be especially well cleaned and, as optically well defined surfaces, contribute to the reduction of scattering losses.

In another embodiment, the concave surface of the sample holder exhibits a roughness of approximately one order of magnitude below the wavelength of the optical radiation. With this roughness, the particles which protrude from the surface serve as condensation nucleation centers for the condensing of the sample substance initially present in solution or emulsion onto the concave surface of the sample holder. Furthermore, with roughnesses below the utilized wavelength of the optical radiation, refraction losses are minimized.

In an improvement of the rotationally symmetric sample holder, the convex surface passes into a conical surface. Such a conical envelope surface is particularly easy to produce.

In another improvement, the convex surface passes into a flat surface, in particular, into a cylinder cover surface. When mounting the sample holder into the spectrometer holder device provided for such a purpose, due to the flat surface, a precise seating of the sample holder and an exact alignment is achieved with respect to the optical axis of the spectrometer.

The invention concerns a method for the accumulation of an absorption spectrum of a powder-like and/or of a sample substance suspended or dissolved in a fluid through transmission measurements with optical radiation in a spectrometer with an optical detector, in particular an infrared spectrometer, whereby with said method, the sample substance is introduced before the measurement onto the surface of a sample holder which is at least partially transparent in the interesting wavelength region of the optical spectrum and the sample holder is then introduced into the optical path of the spectrometer in such a fashion that the sample substance at the sample holder surface carrying the sample substance is positioned largely perpendicularly to the optical path and faces away from the detector.

The object in accordance with the invention of achieving a concentration of the sample substance onto as small an area as possible of the sample holder and to achieve as high an intensity as possible of the light radiated through the sample substance onto the optical axis of the spectrometer is achieved in accordance with the invention in that the sample substance is introduced onto the concave surface of a sample holder of the above mentioned type.

In a particularly preferred embodiment of the method in accordance with the invention, at least a section of the optical path of the spectrometer runs vertically from above to below, and the sample holder is introduced for purposes of the measurement into a vertical portion of the optical path with its concave surface directed upwards. In this fashion, the sample substance on the sample holder is introduced into the spectrometer in a cup and cannot be shaken off. This method is suitable for procedures involving powder-like as well as liquid samples.

In a modification of the method according to the invention in which the sample substance is dissolved or suspended in a fluid, the fluid, before introduction of the sample holder into the optical path of the spectrometer, is completely vaporized or evaporated. In this case, it is no longer necessary to hold the sample holder horizontally in the spectrometer since the sample substance is dried on the concave surface of the sample holder and, in general, can no longer leave the surface even if the sample holder is tipped. Therefore, in this case, the section of the optical path in which the sample holder is introduced for the purposes of measurement can also run horizontally which often allows for a simpler optical alignment of the apparatus.

In another modification of the method, the liquid is only partially vaporized or evaporated before introducing the sample holder into the optical path. In this fashion, the thermal load on a possibly thermally unstable sample substance, in particular, while evaporating the solvent liquid, can be reduced and the time between introducing the dissolved or suspended sample and the measurement can be reduced.

In a preferred improvement of the method, the index of refraction of the liquid is matched to the index of refraction of the sample in the manner of an immersion system.

In an embodiment of the method in accordance with the invention, the fluid in which the sample substance is contained is a low boiling point, easily evaporated solvent, such as, by way of example, alcohol, acetone, etc.

In a particularly preferred embodiment of the method, a first absorption spectrum is initially taken of the sample holder without the sample substance, then a second absorption spectrum with the sample substance brought onto the sample holder and, finally, in a analysis step, the difference between the first and the second absorption spectrum is taken. In this fashion, in particular with quantitative evaluation of the measurement, an increase in the sensitivity level is achieved.

Finally in another embodiment, a plurality of sample holders are simultaneously arranged in a sample changing device, in particular, in a spectrometer sample wheel and a plurality of absorption spectra of various sample holders with or without a sample substance are acquired without any intermediary exchange of the sample holders. In this fashion it is possible to automatically take a whole measurement series of various differing samples as is, by way of example, desired for the purpose of quality control extracted control samples. On the other hand, in a non-automated measurement method, it is possible to measure various sample substances with arbitrary sequences and repetitions without any loss of time due to the introduction and exchange of sample holders.

The invention is more closely described and explained in the following using the embodiment represented in the drawing. The characterizing features which can be extracted from the description and the drawing can be applied to other embodiments of the invention either individually or collectively and in arbitrary combination.

BRIEF DESCRIPTION OF THE DRAWINGS

FIGS. 1(a)–1(f) shows a schematic sectional picture of the sample holder according to prior art (left) and in accordance with the invention (right) with a and d. a fluid drop on the surface of the sample holder containing the sample substance, b and e. a dried sample substance on the surface of the sample holder and c and f. a sample substance irradiated by optical radiation;

DETAILED DESCRIPTION OF PREFERRED EMBODIMENTS

Figure 2A:
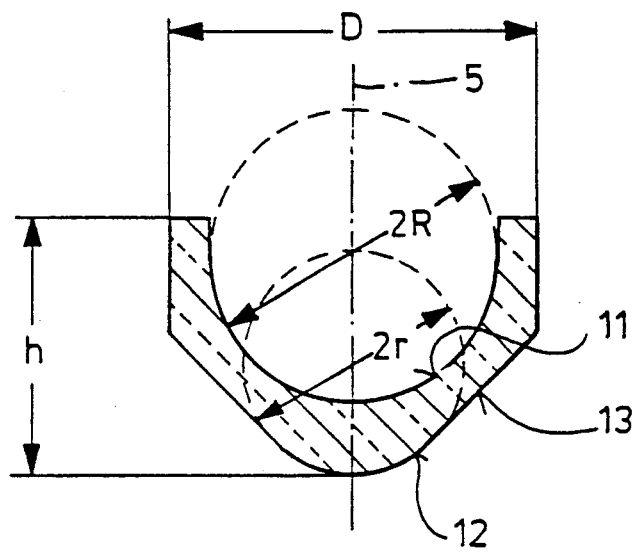
FIGS. 2(a)–(b) shows a vertical cut through the sample holder in accordance with the invention with a convex surface passing into a. a conical surface and b. a cylinder cover surface.

A sample holder shown in the left side of FIG. 1 according to prior art usually consists of a plane parallel plate which is transparent within an interesting wavelength region of the optical radiation in a spectrometer. For the purposes of the transmission measurement, a sample substance which is usually dissolved or suspended in a water solution or in another solvent is brought onto the surface of the sample holder plate (FIGS. 1a and 1d). Subsequently, the fluid, as shown in FIGS. 1b and 1e, is vaporized or evaporated so that the dried sample substance 2 remains in solid-state powder form upon the surface of the sample holder. Disadvantageous thereby is that, after drying, the sample substance is distributed over a relatively large surface area of the flat plate and condenses out preferentially concentrated at the edges of the original drop 1. After insertion in the spectrometer and subsequent irradiation with the optical radiation indicated by an arrow in FIGS. 1c and 1f, a relatively large amount of light is lost for purposes of the absorption measurement due to the disadvantageous distribution of the sample substance on the flat surface of a conventional sample holder. Moreover, there are additional losses due to the fact that the light emanating out of the conventional plane parallel sample holder is, to a large extent, refracted away from the optical axis 5 of the configuration and thereby does not reach the detector 4.

In contrast, the right side of FIG. 1 clarifies how, in the sample holder according to the invention, the drop 1 already forms within a concave surface area 11 which is more spherical and concentrated in shape and, after vaporization of the fluid, the remaining dried sample substance is present upon the concave surface 11 in a more concentrated volume and surface area.

The configuration of the sample holder in accordance with the invention with an additional convex surface 12 exhibiting a smaller radius of curvature than the concave surface 11 has the consequence that the sample holder likewise produced in accordance with the invention from a material which is transparent in an interesting wavelength region works as a focussing converging lens upon irradiation from the sample side with optical radiation 3. After exiting the sample holder in accordance with the invention, the irradiated light is therefore refracted towards the optical axis 5. The light emanating out of the sample holder in the direction of the optical detector 4 of the spectrometer, is thereby, if not already parallel, then at least less divergent. In this fashion, more light from the sample reaches the detector 4 as would have been the case with the conventional flat window.

Since normal optical spectra are, in general, imaged on a slit, it can be useful to arrange the sample holder as a cylindrical lens. For the sample holder cross sections in accordance with the invention of FIG. 1 and FIG. 2, the cylinder axis is then perpendicular to the plane of the drawing. The optical axis 5 is perpendicular to the cylinder axis. The imaging properties of this type of cylindrical lens are optimally matched to the slit-shaped image of a normal optical spectrometer, thereby contributing to an improvement in the light yield. However, a cylinder lens can only effect a convergence of the outgoing light about the cylinder axis so that the converging properties can only be taken advantage of in one dimension. With the cylinder lens, portions of the optical radiation 3 which diverge in the direction of the cylinder axis cannot be redirected towards the optical axis 5.

As mentioned above, this type of sample holder can advantageously be used in relation to chromatography if the cylinder lens is made very long and if necessary even slightly curved.

In another embodiment of the invention the sample holder is configured as a rotationally symmetric converging lens. In this manner, an optimal matching to the imaging geometry of spectrometers with a round aperture, in particular Fourier Transform (FT) spectrometers, is achieved. With the imaging of Fourier Transform spectrometers onto a circular area, in the usual case of flattened extended samples, a better illumination of the, in general, extremely small quantities of sample substance is effected, thereby achieving a significantly improved signal. Through a reduction of the surface extent of the sample substance on the sample holder it is also possible, in the ideal case, to reduce the, in general, rotationally symmetric incident light beam to a light-point at the sample spot.

In particular, when utilizing the sample holder for sample substances which are initially dissolved or suspended in a solvent, the sample holder should be constructed from solvent resistant materials.

ZnSe, in particular in single crystal form, is preferentially proposed as a sample holder material with which the index of refraction of 2.3 is significantly larger than the value 1 for air, thereby effecting a significant convergence of the converging lens, while the reflection losses are nevertheless in the tolerable range of approximately 30%. With the utilization of silicon or germanium with their refractive indices of 3.6 and 4.0 respectively, a particularly strong refraction of the incident light towards the optical axis 5 is achieved, but, due to the high index of refraction, the reflection losses lie in this case in the range of over 50%.

ZnSe is also extremely well suited as a material for the sample holder according to the invention because it is transparent in the wavelength region of 15,000–600 $cm^{-1}$, is not soluble in water, and is chemically inert with respect to most substances.

The concave 11 and convex 12 surfaces of the sample holder can be easily cleaned, highly polished surfaces. In particular, the concave surface 11 offers a well defined optical surface to the incident optical radiation 3 which contributes significantly to minimizing the scattering losses. On the other hand, it is also advantageous when the concave surface 11 has a roughness of approximately one order of magnitude less than the wavelength of the optical radiation 3. In this way, on the one hand, losses due to refraction are minimized and, on the other hand, the particles projecting out of the surface serve as condensation nucleation centers for the condensation of the sample substance after introducing the drop 1 onto the concave surface 11.

Whereas in the method illustrated in FIG. 1 the sample substance is initially brought onto the concave surface 11 of the sample holder dissolved or suspended in a fluid drop 1 and is first present in the form of a dried powder solid 2 only after the complete vaporization or evaporation of the liquid, the sample holder in accordance with the invention can also be utilized for the measurement of sample substances which are already initially in a form of powders, since the concave surface 11 hinders the sidewards slipping of the powder from the surface of the sample. Towards this end it is, however, necessary that the sample holder with the powder to be measured be introduced into a vertical section of the optical path of the spectrometer with the concave surface 11 directed upwards. The same is true in the event that the fluid of a sample substance containing drop is only partially vaporized or evaporated before introducing the sample holder into the optical path of the spectrometer. In this case as well, only a vertical arrangement of the sample holder can prevent the liquid containing the concentrated sample substance from running out.

Such a partial removal of the liquid is, by way of example, particularly reasonable when the index of refraction of the liquid is matched to the index of refraction of the sample in the manner of an immersion system. In any event, it is advantageous to use a liquid with a low boiling temperature which is an easily evaporated solvent, for example, alcohol, acetone, etc. Since, in this event, large amounts of heat must not be introduced to remove most of the liquid from the drop 1, thermally unstable sample substances are, in particular, protected.

A disadvantage of the immersion system described above is the usual strong spectral banding of the solvent which interferes with the sample substance measurement values of interest. For this reason, it is advantageous in the immersion method if the fluid is, to a large extent, vaporized or evaporated so that the sample substance is present in a very high concentration and the signal emanating from the sample substance projects clearly above the background caused by the solvent.

In the event that the spectrum taken is to be quantitatively analysed, it is advisable to subtract the empty spectrum of the sample holder in order to increase the sensitivity level. Towards this end, a first absorption spectrum is initially taken of the sample holder without the sample substance, then a second absorption spectrum is taken with the sample substance on the sample holder, and finally, the difference between the two spectra is formed.

Vertical cross sections of two examples for the shape of a sample holder according to the invention are shown in FIG. 2. The sample holder according to FIG. 2a, in which, for the case of a rotational symmetric configuration, the convex surface 12 passes into a conical surface 13 is particularly easy to manufacture. In the event of a cylinder lens configuration, the surfaces 13 are flat surfaces and the sample holder has the general form of a groove.

Figure 2B:
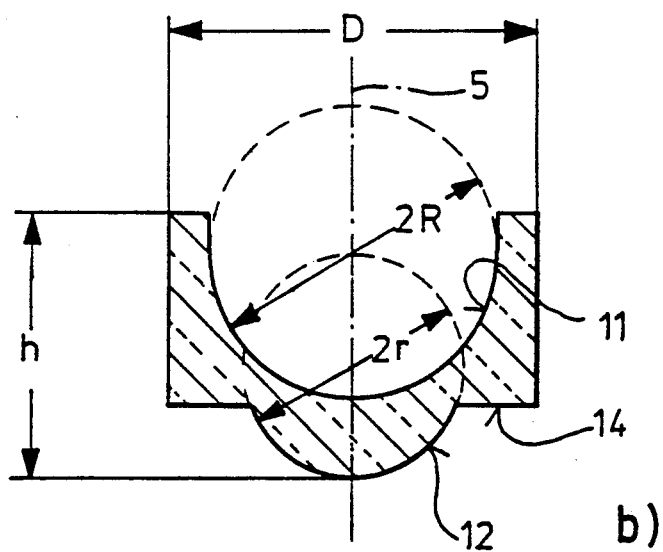

Shown in FIG. 2b is a sample holder with which, for the case of a rotationally symmetric configuration, the convex surface 12 passes into a cylinder cover surface 14 and, for the case of a cylindrical lens sample holder configuration, into two right rectangular plane surfaces 14. This shape enables a precise seating of the sample holder onto the plane surface 14 when aligning the sample holder in the spectrometer.

Embodiments of the sample holder shown in FIG. 2 were produced with an outer diameter $D=5$ mm, a height $h=3.5$ mm, a radius of curvature $R=2$ mm for the concave surface 11, and a radius of curvature $r=1.5$ mm for the convex surface 12 and were utilized for measurements.

For experimental comparison to conventional sample holders known in the art, glycine and anthracene were chosen as standard substances. Glycine with its strongly polar binding and anthracene with its strongly unpolar binding should represent a wide region of substances. The associated anthracene and glycine infrared spectra shown in FIG. 3 and FIG. 4 respectively were taken with a ZnSe sample holder according to the invention and are directly compared to the spectra taken under analogous conditions of the same corresponding substances using the established KBr press technique. Thereby, a KBr powder of about 1 volume % powdered sample material was mixed in and, in order to take a spectrum, the mixture was pressed into a sheet of about 0.5 to 1 mm thickness. A substantial advantage of the procedure according to the invention is the avoidance of this substantial amount of work which is necessary in the conventional KBr press technique.

Figure 3:
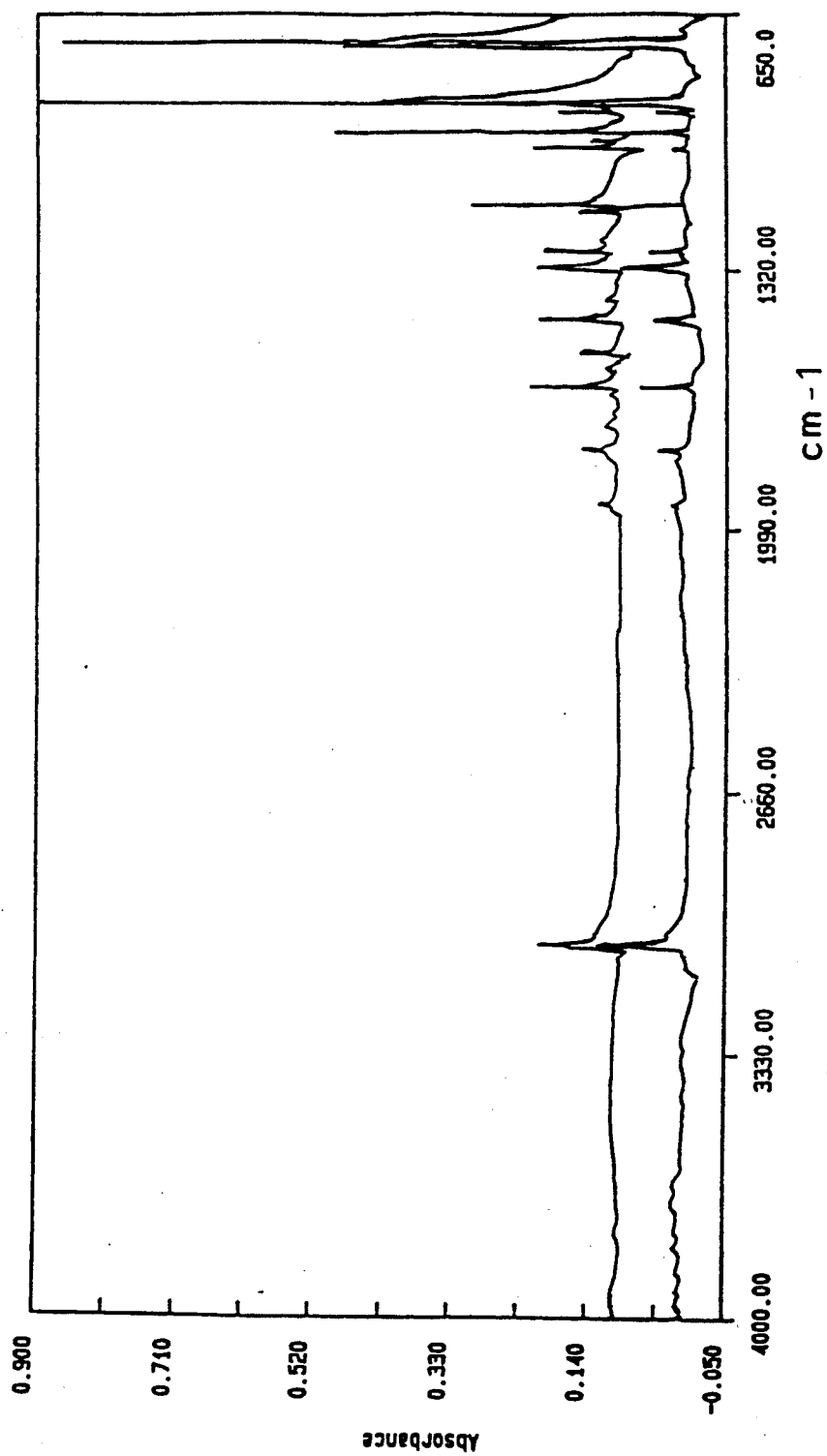
FIG. 3 shows two absorption spectra of anthracene with a sample holder in accordance with the invention made from ZnSe (below) and a conventional sample holder of the KBr-pressing technique variety (above)

The normalized anthracene spectrum taken with KBr is compared to the normalized anthracene spectrum taken with ZnSe in FIG. 3. For the unpolar aromatic anthracene, one sees that the band positions and the intensity distributions are nearly identical in both spectra. Differences are noticeable only in the band shapes. The KBr spectrum is distinguished by asymmetric signals led by more frequent negative banding. These interfering manifestations, also known as the Christiansen effect, are not present in the spectrum taken with ZnSe.

Figure 4:
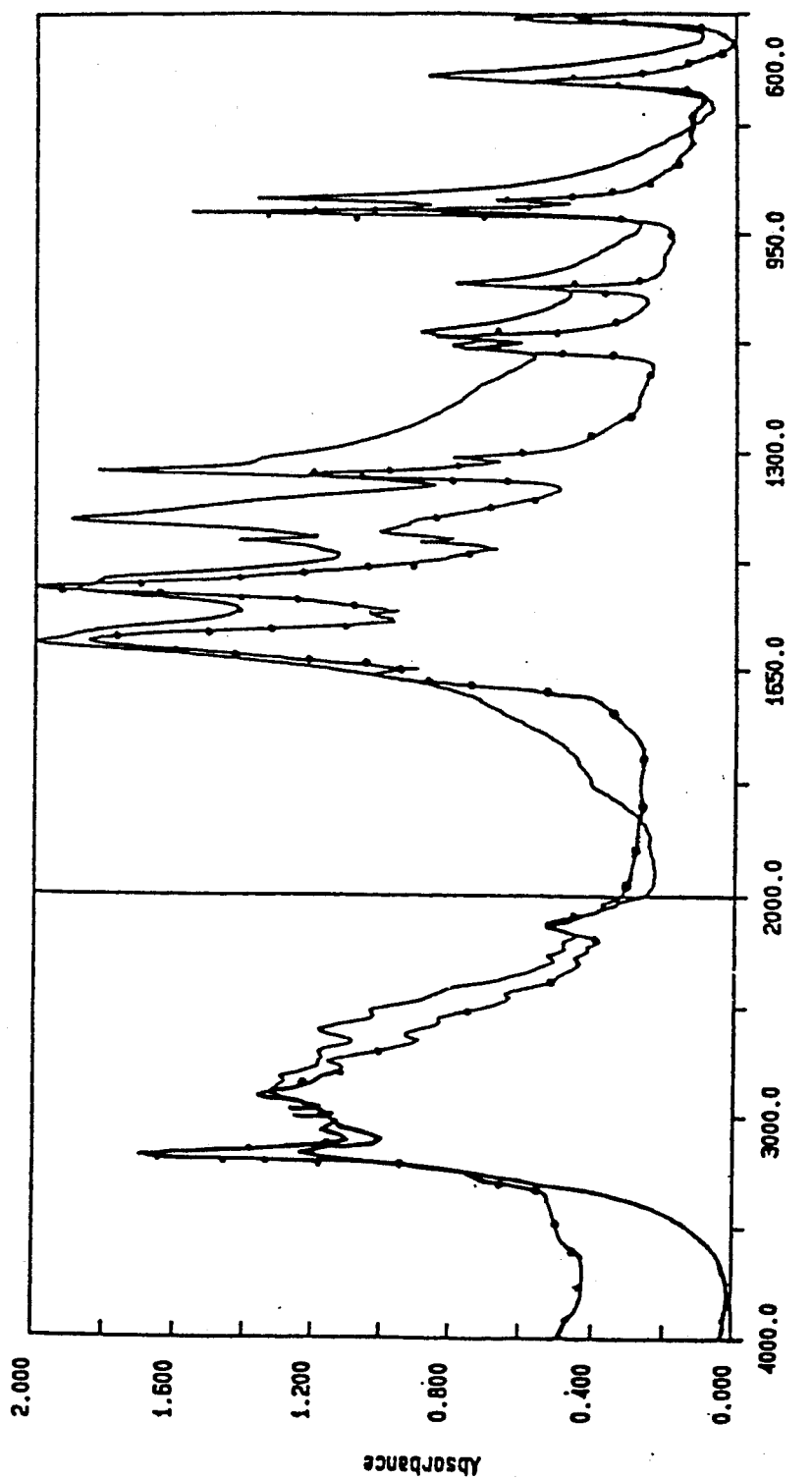
FIG. 4 shows an absorption spectrum of glycine with a ZnSe sample holder (with points) in accordance with the invention and with a sample holder of the KBr-pressing technique variety (solid lines)

A glycine spectrum with KBr is compared to a normalized spectrum with ZnSe in FIG. 4. Here one notices, in particular, the steep prominent structure in the spectrum of the sample holder according to the invention which contributes to an improved separation of the characteristic peaks and, thereby, to an improved resolution in the spectrum. In the wavelength region from 1,400 to 600 $cm^{-1}$ all bands of the spectrum taken with ZnSe are shifted on the average by approximately 4 $cm^{-1}$ in the direction of larger wave numbers. The cause of this difference between the two spectra is most likely associated with the differing strong interactions of the polar amino acid glycine with the respective matrix of the sample holder material. In the case of the KBr pressing technique, strong intermolecular interactions occur between the glycine and the KBr in consequence of their very similar polarities. An associated influence on the vibrational structure leads to somewhat changed excitation frequencies. In contrast, the interaction between Glycine and ZnSe is relatively small. On the one hand, there is no intermixing as in the case of the KBr press technique and, on the other hand, the polarity of the ZnSe is significantly less than that of KBr. In this manner, both the differences in the glycine spectra and the good quantitative agreement between both anthracene spectra are simultaneously accounted for.

In general, the comparison shows that the spectral content of the ZnSe spectra is very similar to that of the KBr spectra. The absence of the Christiansen effect in the ZnSe measurement technique is of great advantage. In consequence of the reduced matrix interactions, it could be conceivable that the ZnSe measurement technique of polar substances would, in general, effect IR spectra with somewhat higher resolution. In any event, the amount of work necessary to take a spectrum is significantly less in the method according to the invention.

Figure 5:
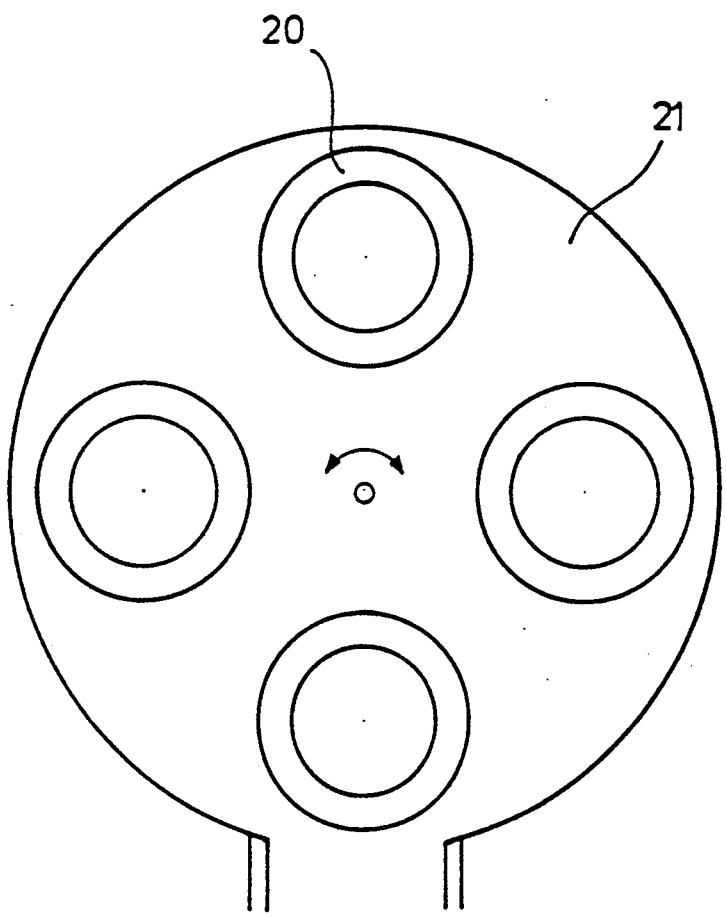
FIG. 5 shows a sample wheel with a plurality of sample holders.

To take a large series of measurements and to accept different samples without intermediate exchange of the individual spectrometer sample holders, it is possible for a plurality of sample holders 20 to be simultaneously arranged in a sample changer device, by way of example, in the usual sample wheel 14 of the spectrometer as shown in FIG. 5. Thereby, it is recommended that one holder position is provided for on the sample wheel 21 for the taking of a background spectrum. In this manner, it is possible to automatically take a complete measurement series of differing samples in a predetermined sequence as can, by way of example, be desirable for fast quality control of control samples from, by way of example, a manufacturing process. On the other hand, it is also possible via appropriate electronics or mechanical devices to individually select and identify the corresponding sample wheel positions so that, without any substantial loss of time, spectra from different samples can be taken or repeated in arbitrary sequence and with arbitrary frequency.

The reference numbers in the following claims do not signify limitations, rather are intended to facilitate understanding.

We claim:

1. Sample holder for the introduction of a sample substance for transmission measurements with optical radiation in a spectrometer, said sample holder having an optical axis and comprising a converging lens having means defining a concave surface, with a radius of curvature R, for receiving the sample substance and means defining a convex surface, with a radius of curvature r, for refracting the optical radiation passing through the sample substance and the concave surface toward the optical axis such that the optical radiation becomes less divergent or parallel, said sample holder being formed, at least in part, from a material transparent to the optical radiation and having an index of refraction in excess of 1 and the convex radius of curvature r is less than the concave radius of curvature R.

2. Sample holder according to claim 1, wherein the sample holder is configured as a cylinder lens.

3. Sample holder according to claim 1 wherein the sample holder is configured as a lens rotationally symmetrical about an optical axis.

4. Sample holder according to claim 3 wherein the sample holder is configured for a Fourier transform infrared spectrometer.

5. Sample holder according to claim 1 wherein the sample holder is configured from material which is solvent resistant.

6. Sample holder according to claim 5 wherein the sample holder is at least partially constructed from ZnSe.

7. Sample holder according to claim 1 wherein the concave surface and the convex surface are polished.

8. Sample holder according to claim 1 wherein the concave surface exhibits a roughness of about one order of magnitude below the wavelength of the optical radiation.

9. Sample holder according to claim 3 wherein the convex surface abuts a conical surface.

10. Sample holder according to claim 3 wherein the convex surface abuts a plane surface.

11. Method for taking an absorption spectrum of a sample substance through transmission measurements with optical radiation in a spectrometer with an optical detector comprising the steps of introducing the sample substance onto a concave surface of a sample holder having an optical axis and which is at least partially transparent to the optical radiation in an interesting wavelength region, introducing the sample holder into an optical path of the spectrometer in such a way that the sample holder concave surface carrying the sample substance is essentially perpendicular to the optical path thereof and faces away from the detector and refracting optical radiation passing through the sample holder with a convex surface on said sample holder towards the sample holder optical axis.

12. Method according to claim 11 wherein the optical path of the spectrometer runs at least section-wise vertically from above to below and that the sample holder, for purposes of measurement, is introduced with its concave surface directed upwards into a vertical section of the optical path.

13. Method according to claim 11, whereby the sample substance is dissolved or suspended in a fluid and the fluid is completely brought into a gaseous state before introducing the sample holder into the optical path.

14. Method according to claim 12, whereby the sample substance is dissolved or suspended in a fluid and the fluid is only partially brought into a gaseous state before introducing the sample holder into the optical path.

15. Method according to claim 14 wherein the index of refraction of the fluid is matched to the index of refraction of the sample in the manner of an immersion system.

16. Method according to claim 11 wherein the fluid is a low boiling point, easily vaporized solvent.

17. Method according to claim 11 wherein a first absorption spectrum is initially taken of the sample holder without a sample substance, a second absorption spectrum is taken with the sample substance brought onto the sample holder, and thereafter, in an analysis step, the difference between the first and the second absorption spectra is formed.

18. Method according to claim 11 wherein a plurality of sample holders are simultaneously arranged in a sample changer device in the spectrometer, and a plurality of absorption spectra from various sample holders are taken without any intermediate exchanging of the sample holders.

* * * * *